(12) United States Patent
Schierholz

(10) Patent No.: US 6,641,831 B1
(45) Date of Patent: Nov. 4, 2003

(54) MEDICAL PRODUCTS WITH SUSTAINED PHARMACOLOGICAL ACTIVITY AND PROCESS FOR PRODUCING THEM

(76) Inventor: Jörg Schierholz, Neuer Trassweg 11, Bergisch Gladbach (DE), 51427

(*) Notice: Subject to any disclaimer, the term of this patent is extended or adjusted under 35 U.S.C. 154(b) by 0 days.

(21) Appl. No.: 09/762,318

(22) PCT Filed: Aug. 5, 1999

(86) PCT No.: PCT/EP99/05685

§ 371 (c)(1),
(2), (4) Date: Apr. 6, 2001

(87) PCT Pub. No.: WO00/07574

PCT Pub. Date: Feb. 17, 2000

Related U.S. Application Data

(60) Provisional application No. 60/095,562, filed on Aug. 6, 1998.

(30) Foreign Application Priority Data

Aug. 6, 1998 (DE) .......................... 198 35 546
Aug. 6, 1998 (EP) .......................... 981147812

(51) Int. Cl.⁷ ............................... A61F 13/00
(52) U.S. Cl. ................ 424/422; 424/423; 424/424; 424/425; 424/484; 424/486; 424/487; 424/488; 514/772.1
(58) Field of Search .................. 424/422, 423, 424/424, 425, 484, 486, 487, 488; 514/772.1

(56) References Cited

U.S. PATENT DOCUMENTS 4,191,743 A * 3/1980 Klemm et al. ............ 424/28
4,642,104 A * 2/1987 Sakamoto et al. .......... 604/264
4,713,239 A  12/1987 Babaian et al. ............ 424/81
4,882,167 A * 11/1989 Jang ........................ 424/468
5,357,636 A * 10/1994 Dresdner, Jr. et al. ........ 2/161

FOREIGN PATENT DOCUMENTS

EP    0 184 629 A2    6/1986
EP    0 328 421 A2    8/1989
WO    WO 96/33670    10/1996
WO    WO 96/38174    12/1996
WO    WO 97/25085    7/1997

* cited by examiner

Primary Examiner—Thurman K. Page
Assistant Examiner—Liliana Di Nola-Baron
(74) Attorney, Agent, or Firm—Jacobson Holman PLC

(57) ABSTRACT

A non-degradable medical product comprising at least two substances or groups of substances, of which a first substance is referred to as substance A and a second is referred to as substance B, substance A being more lipophilic than substance B, wherein substance A has a solubility (w/w) in water of from 300 μg/ml to 1 μg/ml, substance B has a higher solubility than that of substance A, at least one of substance A and B is a pharmaceutically active substance, and wherein the amount of substance A or B is respectively from at least an effective amount to 10% by weight, based on the weight of the support material;
with the exception of the combinations chlorohexidine/silver sulfadiazine, tri-closane/chlorohexidine, polyethylene gltcol/polyurethane, porous polyethylene with combinations of clotrimazole and triclosane.

19 Claims, 5 Drawing Sheets

MEDICAL PRODUCTS WITH SUSTAINED PHARMACOLOGICAL ACTIVITY AND PROCESS FOR PRODUCING THEM

This application claims the benefit of provisional application No. 60/095,562 filed Aug. 6, 1998.

The present invention relates to medical products with sustained pharmacological activity and a process for producing them.

DE-A-36 13 213 discloses an absorbable porous tricalcium phosphate with a mixture of an antibiotic and another filler, especially a hydrophilic amino acid, as being particularly advantageous for the preparation of bone cements. A low-molecular weight additive is incorporated in the tricalcium phosphate: glycine, which is water-soluble and accelerates the release of the active ingredient from the porous tricalcium phosphate.

WO 84/03623 discloses magnesium oxide, hydroxide or other magnesium salts which have effects on the release from tablets with calcium antagonists.

WO 89/09626 discloses a hydrogel coated flexible tube which is loaded with polymyxin and which is to prevent that polymyxin-sensitive microorganisms form thrombi or induce an infection.

U.S. Pat. No. 4,612,337 describes a method in which plastic materials are soaked in solutions containing various active substances, for example, ethanol, chloroform, and the thus surface-coated materials are later dried and induce a short-term release of active substances.

EP-A-0 520 160 describes the swelling of polyurethane catheters with fluorinated hydrocarbons in which quarternary ammonium salts are incorporated by such process. After drying, the catheters are to become antimicrobially active through release.

DE-A-37 25 728 describes a method in which silver metal ions are added to polyurethane silicone mixtures. Through the mixing of polyurethanes with silicone, body fluid is supposed to penetrate in the mixture of plastics and thus wash out the silver ions, which is to have an improved germicidal effect.

WO 89/04628 discloses the treatment of silicone implants with antibiotics and chloroform such that the active substances can diffuse into the outer layers of the implant material and thus a short-time release of active substances is provided after the implantation of the finished device.

WO 87/03495 describes exactly the same method as WO 89/04628, with a drawing illustrating how catheters can be impregnated.

EP 0 484 057 A2 describes an aqueous coating for rendering medical products antithrombogenic by mixing organic polymers, binders, spacers and heparin as the antithrombogenic agent with methylene/acrylic acid copolymer and colloidal silicates. This resin may also be preliminarily sulfonated before this resin coating is applied to the medical products.

U.S. Pat. No. 4,642,104 discloses a urethral catheter made of an olefinic polymer or a silicone material in which antimicrobial substances are bound on the outside and inside.

U.S. Pat. No. 4,677,143 describes antimicrobial mixtures for coating medical products. These mixtures consist of acrylonitrile block polymers, polyvinyl chloride, mixtures of polyesters and polyurethanes, styrene block copolymers and natural rubbers and polycarbonates, nylon and silicone materials which are mixed with oligody-namic substances, i.e., antibacterial metals, preferably silver oxide compounds. These catheters were examined in a clinical test with 1,300 patients. No difference as compared to uncoated catheters was found (Riley et al., 1995, Am. J. Med.).

WO 87/01595 discloses how antimicrobially active substances, antibiotics, are added to plastic materials prior to the chemical polymerization process. The active substance is uniformly distributed in the plastic material prior to polymerization. Application example: Fixateur externe.

WO 95/04568 describes injection ports which include antimicrobial substances, for example, chlorhexidine, silver sulfadiazine and others.

U.S. Pat No. 5,525,348 discloses coatings with polyvinylpyrrolidone in different solvents, followed by the addition of various other oligomers with heparin benzalkonium chloride which yield ionic surfactant coatings.

EP 0 640 661 A2 describes mixtures of silicone with silver-containing zeolites, the silver ions diffusing out of these zeolites.

EP 0 301 717 B1 also describes zeolites which are incorporated in medical plastics. These zeolites comprise silver, copper or zinc which are incorporated by kneading and are to achieve the antimicrobial effect.

EP 0 470 443 B1 discloses how thin coatings are applied, for example, to catheter materials at low extrusion temperatures together with temperature-sensitive pharmaceutical ingredients.

U.S. Pat. No. 5,451,424 describes lamination processes via the extrusion of plastics by which medical products are coated with medicaments on the outside and inside thereof.

WO 92/01542 describes how coatings for nasootopharyngial tubes are prepared by "solvent casting", i.e., immersing the medical products in a solution of plastics in which medicaments are dissolved, for example, in order to prevent chronic infections and inflammations of the surrounding tissue.

WO 96/39200 describes that a metal salt can be incorporated in a plastic matrix by "solvent casting".

U.S. Pat. No. 4,999,210 describes how a homogeneous melt of plastics and chlorhexidine is prepared, and the mixture is coextruded onto medical articles through a twin-screw compounder. These articles are later again placed in a dipping solution (solvent casting) with a hydrophilic polymer.

EP 0 350 161 A2 discloses how a substrate is coated with an ammonium salt and then heparinized at an alkaline pH value.

WO 91/01767 describes how ammonium heparin complexes are applied to medical plastics by "solvent casting" using dichloromethane, isopropanol and other solvents.

EP 0 231 573 B1 describes that pharmaceutical substances are incorporated in solid plastics by either solvent casting or adsorption by swelling.

U.S. Pat. No. 5,514,673 describes a pharmaceutical composition in which clinical effects are achieved by transmucosal administration of progesterone or 17-β-estradiol. Thus, 3 μg to 0.5 mg of 17-β-estradiol or progesterone is mixed with natural oils, and egg lecithin is added. These mixtures are to be administered via the nose and produce effecs there. This method is to reduce skin irritations, with lecithin acting as a solubilizing agent.

WO 96/32907 describes a metallic stent with a hydrophobic elastomeric plastic layer in which a biologically active substance is incorporated. The method involves "solvent casting". Heparin is preferably used at a weight proportion of from 10 to 45%, with a layer thickness of between 30 and 150 μm, and dexamethason with a proportion of between 0.5 and 10%.

WO 96/39215 describes how a silicone flexible tube is produced which has a layer with pharmacologically active substances inside the material which slowly diffuse outwards through the uncoated outside layer. A sandwich catheter is produced using a silicone extrusion machine. Rifampicin and minocyclin are introduced in the intermediate layer as powders.

WO 96/33670 discloses how antimicrobial mixtures, preferably rifampicin/minocyclin mixtures, are incorporated in medical plastics by swelling and increasing the temperature followed by alkalizing the solution.

WO 94/10838 describes solutions with minocyclin-EDTA with which medical products are rinsed in order to prevent infections.

U.S. Pat. No. 5,688,516 describes mixtures of pharmaceutical substances which contain the three above mentioned groups of active substances, i.e., anticoagulants, antithrombotics and complexing agents, such as EDTA or DMSA. These active substances are to be applied to medical products precoated with TDMAC.

WO-A-96/33670 relates to catheters and medical implants impregnated with antimicrobial substances, and a method for impregnating these medical products. First, an antimicrobial composition is prepared with an effective concentration of the active ingredient to prevent the growth of organisms, followed by applying this composition to at least part of the medical product and permeating of the composition into the material of the medical product. The composition is prepared by dissolving the antimicrobial agent in an organic solvent with the addition of a penetration agent and an alkalinizing substance.

WO-A-97/25085 relates to medical products containing triclosane.

U.S. Pat. No. 4,713,239 relates to a medical product consisting of a support material which is a homopolymer of acrylamide or vinyl pyrrolidone or a copolymer thereof with acrylate containing from 99 to 70% of acrylamide with vinyl pyrrolidone and from 1 to 30% by weight of acrylate having a molecular weight of from 50,000 to 1,000,000, and an active ingredient having antianginal activity, the components being contained in the following amounts: active ingredient having antianginal activity: from 3 to 30% by weight; biologically soluble and absorbable support: from 70 to 97% by weight.

EP-A-0 328 421 relates to an infection-resistant composition, medical products and surfaces, and methods for the preparation and use thereof. The infection-resistant medical product disclosed therein comprises one or more matrix-forming polymers selected from the group consisting of biomedical polyurethanes, biomedical silicones and biodegradable polymers, and antimicrobial agents, especially a synergistic combination of a silver salt and chlorohexidine or a salt thereof. Also disclosed are medical products having synergistic compositions therein or on the surface thereof.

Allogenic implant materials are essential in modern medical engineering. The advantages achieved with such medical products, i.e., medical products such as peritoneal catheters, cardiovascular plastic products, orthopedic implants or other prosthetic implants, are impaired by infectious complications or thrombotic events or other secondary side-effects. The main pathogens causing infections of plastic implants are *Staphylococcus epidermidis* and *Staphylococcus aureus*. These germs are responsible for 70 to 80% of all infections with vascular catheters. *Candida albicans* is responsible for 10 to 15% of all catheter infections. In urinary tract infections (UTIs), it is considered that the use of urinary catheters, such as Foley catheters, suprapubic and nephrostomy catheters is associated with most of these infections. Such catheters are often implanted in older patients, patients suffering from paralysis of the urogenital tract, postoperative patients and those suffering from obstructive uropathy.

Despite of all sterile precautions being taken in the insertion and open-keeping of all these catheters, these infections remain a serious problem. With a proportion of 60 to 70%, Gram-negative bacteria are the main pathogens of urinary tract infections, followed by enterococci and Candida. In the case of metallic prostheses, due to the advanced surgical technique, the relative number of infections is very much lower than with catheter materials. However, since these infections can only be remedied by an explantation of the infected materials and the costs of remediation and reimplantation and the mortality of older patients are very high, preventive measures are indispensable from an economical and medical point of view.

Much the same applies to vascular prostheses; in this case, infection rates of between 1 and 3% are expected for inguinal vascular prostheses, which are in addition reimplanted with essentially higher infection rates after an existing prosthesis having been infected. The problem consists in the high mortality, being up to 50% of the patients, and the high amputation rate of the distally concerned extremity. Another problem with all medical products such as central venous catheters, intracoronary stents, cardiac valves (Olenoff (1)), absorbable wound plasters, CAPD catheters, spun-bonded webs or vascular prostheses is thrombogenicity. The thrombogenic potential of foreign body materials can be reduced, in principle, by modification with antithrombogenic medicaments.

A third group of indication fields are ocular implants, in which antiinfective and antihypertensive agents are advantageous as coating substances. Other indication fields are the prevention of incrustation by the release of complexing agents from urinary tract catheters, and the controlled release of hormones, antihormones, cytostatics and peptides from cements, prosthetic materials, pacemakers, stents and other materials.

A known method for the modification of medical products comprises applying a layer of tridodecylmethylammonium chloride (TDMAC) surfactant and then antimicrobial substances which are Ionically charged to the surface of catheters. For example, polyethylene/silicone Elastomers, polytetrafluoroethylene or Dacron materials can be soaked in 5% TDMAC solutions for 30 minutes, dried and rinsed. These TDMAC surfactant bearing medical products can then be incubated in solutions of various active substances.

A similar procedure may be applied to benzalkonium chloride and the ionic binding of antimicrobial substances (Solomon D. D., Sheretz, R. E. J., in j. Contr. Release 6: 342–352 (1989), and U.S. Pat. No. 4,442,133).

Other methods include the ionic binding of active substances having negatively charged groups to the surface of medical products (U.S. Pat. No. 4,895,566);

the swelling of medical products and adsorption in the surface (U.S. Pat. No. 4,917,686);

the preparation of ionic hydrogels which later bear tonically bound active substances (U.S. Pat. No. 4,107,121);

the lamination of antimicrobial substances to surface layers (U.S. Pat. No. 5,013,306); or even the mere application of a silicone oil to a medical product followed by contacting the silicone film with a solution of an active substance (U.S. Pat. No. 4,952,419).

One drawback of these methods is that the activity of the active substance subsides relatively quickly due to such physico-chemical methods. As to antimicrobial effectiveness, for example, catheters or vascular prostheses or other implants can again be colonized by bacteria after their bactericidal surface activity has decreased. The same applies to the coating with antithrombogenic agents. Clinical efficiency is to be expected only if active substances are releases in sufficient amounts. Much the same applies to antiproliferative and proliferative substances. A drawback of these coatings is the lack of an efficient control of the release of the pharmaceutical substances from the medical products (4). To achieve constant effects over a prolonged period of time, it is desirable to closely approach an idealized release of zero order.

Vascular prostheses and metallic implants (e.g., TEPs) can be modified with antibacterial, antithrombotic, antiinflammatory, immunomodulating or endocrinically active substances with or without spacers (albumin, collagen, biodegradable coatings).

The object of the present invention is to provide non-degradable medical products which are pharmacologically active, and to provide methods for sustaining a pharmacological activity as long as possible and thus to overcome the mentioned drawbacks of the prior art. Another object of the invention is to provide a practical, cost-effective, safe and efficient method for modifying a wide variety of catheter types and other medical products with various combinations of substances. One object of this invention has been, inter alia, to protect medical products from infections as long as possible using different incorporation and coating methods.

This object is achieved by a non-degradable medical product comprising a support material, two substances or groups of substances, of which the first is referred to as substance A and the second is referred to as substance B, substance A being more lipophilic than substance B, wherein substance A has a solubility (w/w) in water of from 300 $\mu$g/ml to 1 $\mu$g/ml, substance B has a higher solubility than that of substance A, at least one of substances A and B is a pharmaceutically active substance, and wherein the amount of substance A or B is respectively from at least an effective amount to 10% by weight, based on the weight of the support material, with the exception of the combinations chlorohexidine/silver sulfadiazine, triclosane/chlorohexidine, polyethylene glycol/polyurethane, porous polyethylene with combinations of clotrimazole and triclosane. A lower solubility can have both kinetic and thermodynamic reasons. The solubility is measured, for example, at room temperature (about 25° C.), pH 7.

Surprisingly, it has been found that, in a non-degradable polymeric matrix, a monolithic distribution of two substances having different degrees of hydrophilicity results in a retardation of the release of the hydrophilic component when a hydrophilic substance is combined in a dispersed state in the polymer (up to 10% by weight) with a hydrophobic substance (up to 10% by weight). This effect is produced physicochemically by the interaction of the active substances on a molecular level to achieve a reduction of the diffusion rate; there is no degradation of the polymeric matrix and thus no further influence on the release. It was further surprising to find that the association of two active substances by salt formation (miconazole base/fusidinic acid, Ag-EDTA) enhances the retardation by the lipophilic component.

According to WO-A-96/38174, microencapsulated and homogeneously distributed substances can control release in a biologically degradable polymeric matrix, mainly controlled by the disintegration of the polymer matrix. Biological degradation facilitates the release of substances by the breaking of molecular bonds in the support material and enables the formation of pores, cavities by the penetration of external medium (blood, cerebrospinal fluid, urine). The active substances are released from the association by convection, degradation, dissolution and also diffusion. If the polymeric matrix is additionally crystalline, as described in WO-A-96/38174, diffusion of the active substance through crystalline polylactide is nearly impossible, and thus the release of the active substance is almost exclusively controlled by the rate of biodegradation. In this case, influencing the release by selecting the substances is possible only if more substance is present as compared to the matrix (preferred range of from 30 to 80 mass percent).

In the present invention, however, this is possible already with a 1–20% proportion of active substance for stable medical products.

In addition, it has been surprisingly found that the retardation effect was enhanced by a gradient formation of the lipophilic substance, based on the ratio of surface concentration to bulk concentration (matrix concentration), if more lipophilic substance was deposited on the surface. This may be effected, for example, by extracting a charged medical product with a solution of the lipophilic component in a suitable solvent, whereby more lipophilic substance is deposited on the surface, and hydrophilic substance is extracted.

Surprisingly, it has been found that the sparingly soluble substance itself can act as a support matrix and depot for sustaining release (see Example 6). Thus, paints can be applied to non-degradable implant surfaces which are only composed of a lipophilic and a hydrophilic component.

The sustaining effect is most pronounced for an excess of the lipophilic component as compared to the hydrophilic component, and for solubilities of the lipophilic component of from 100 $\mu$g/ml to 1 $\mu$g/ml.

The solubility is the maximum amount of a substance which is soluble in water at 25° C. The weight of the substance is calculated based on the total weight of the solution obtained. Within the scope of this application, substances with low solubility are also characterized by the property of being "lipophilic". Suitable medical products are, for example, metallic and non-metallic medical products, such as endoprostheses, knee prostheses or catheters and drains and other polymeric medical products which are modified with a combination of pharmaceutically active substances using a variety of methods. By the modification with pharmaceutical substances, the medical products are to a) become more infection-resistant or b) more hemo- or biocompatible or c) the ultimate function of the medical product or its integration in the surrounding tissue is to be improved or other specific pharmacological effects are to be achieved. The combination of at least two different substances is essential to the coating, impregnation or other modification of medical products, wherein one substance has a low solubility in water and the second substance has a higher solubility in water. This results in substance A having a lower solubility in the surrounding medium (cerebrospinal fluid, blood, urine, tissue or peritoneal fluid) than in the polymer, or is so sparingly soluble that the dissolving processes in different body fluids enable a prolonged release phase, as it may also be the case with only superficially coated total endoprostheses. Surprisingly, substance A having a low solubility causes the release of the other substance, B, to be sustained, i.e., decelerated. By such deceleration of the release of substance B, a so-called "steady state release" profile is obtained in which an almost constant release is achieved after a very slight initial decrease of release. Especially if substance B is an active substance, the thus modified medical products are capable of exhibiting a sustained pharmacological action.

In the following, the invention is illustrated by the example of a combination which is limited to a substance A and a substance B. One skilled in the art will understand that more than one substance from the respective groups may be present.

The very low solubility of substance A in the later implantation tissue (blood, cerebrospinal fluid, urine, peritoneal fluid, tissue fluid) provides a sustained, prolonged release of this substance. It is surprising that, due to the sustained release of this substance A, the release of a substance B which is normally released very much faster is also sustained. Firstly, substance A surprisingly acts as a depot for itself, i.e., as a reservoir which dissolves very slowly little by little, and secondly, it surprisingly acts as a diffusion matrix for substance B, which would be released very much faster within a short period of time without the diffusion matrix. However, the solubility of substance A must not be so low that substance A is virtually insoluble because pharmacologically effective concentrations are not attained then in the surrounding medium. For example, silver chloride is unsuitable. It may be that only one of substances A and B is an active ingredient, or preferably both substances are active ingredients. Preferred active ingredients have antimicrobial, antithrombogenic, antiproliferating, immunomodulating and/or endocrine properties. A loading of at least 0.1% by weight of both of the substances has proven useful in order to produce pharmacological effects in the microenvironment of the medical product for an extended period of time. When substance A is mixed with substance B, it has proven useful for substance A to have a proportion of more than 0.1% (order of magnitude) of the whole substance. Very much lower proportions of the combination no longer have the desired sustaining effect. As a rule, the sustaining effect increases as the incorporation rate and the proportion of substance A increase.

It is preferred for the active ingredient not to have a high solubility in aqueous media, i.e., to be lipophilic. If the carrier matrix is not sufficiently lipophilic, a lipophilization of hydrophilic active substances can be achieved by lipophilizing the active substances by covalent or non-covalent modification, such as by esterification, etherification, acetal or semiacetal formation, ring formation, adduct formation, or in a non-covalent form by complex or salt formation. For example, gentamicin salt or gentamicin base can be modified with a lipophilic fatty acid to increase. lipophilicity. The same applies to erythromycin stearate or clindamycin palmitate and many other pharmaceutical substances the galenics of which can thus be changed.

It is preferred for the active substance to become intracellularly enriched in the target organs or organisms (e.g., bacteria, platelets). Examples include the intracellular enrichment of rifampicin or erythromycin, fusidinic acid, imidazole or clindamycin derivatives in bacteria. The same applies to the lipophilic mupirocin and quinolone derivatives. However, much the same also applies to lipophilic active ingredients, such as ticlopidin, which may become enriched in platelets.

It is particularly preferred for substances A and B both to be active substances which become enriched in cells.

Suitable medical products are eye lenses, catheters, vascular prostheses, endoprostheses, surgical antimicrobial drug carriers, such as collagen web, stents, blades, bone cement, metallic endoprostheses, knee prostheses, hip prostheses, CAPD catheters, wound plasters, sprayed polyurethane webs, drains, bone/soft tissue substitutes.

Preferred materials for the medical products are siloxanes, polyurethanes, acrylates, polycarbonates, cellulose, cellulose derivatives, polymers of tetrafluoroethylene and polyethylene terephthalate.

The present invention further relates to a medical product according to claim 1, characterized in that substance A is a pharmaceutically active substance.

The substances can be combined with the medical products in a wide variety of ways. A highly efficient modification of medical products is effected by swelling with suitable solvents and suitable swelling partners as described in EP 0 550 875. Because the solubility parameters (Hansen parameter, cohesive energy densities) of polymer and pharmaceutical substance are similar, sufficiently high concentrations of active substances are achieved in medical products. The thus loaded medical products become pharmacologically active through controlled release of the active substances from these medical products.

Examples thereof include the swelling of polyurethanes with alcohols, acetone, ketones, esters, such as ethyl acetate, for selected aromatic polyurethanes with $CH_2Cl_2$, DMF, DMA, methyl ethyl ketone, HMPT, DMSO, dioxane (hot), m-cresol, tricresol, n-propanol, dichloroacetic acid or mixtures thereof.

Examples of suitable combinations of pharmaceutically active substances, swelling agents and polymers can be seen from the following table.

| Substance | Swelling agent | Polymer |
|---|---|---|
| cyclophosphamide | ethanol, chloroform, toluene, acetone, dioxane | PUR, PDMS, polycarbonate, polyethylene |
| tamoxifen | choloform, hexane | PDMS, PMMA, polyethylene |
| buselerin | methanol, ethanol | PUR, polycarbonate, cellulose |
| ketoconazole | chloroform, methanol | PDMS, PMMA, polycarbonate, polyethylene |
| diclofenac | DMF, ethanol | PUR, polycarbonate |
| indometacin | chloroform | PMDS, PMMA |
| ibuprofen | chloroform, ethanol, acetone, ether | PMDS, PMMA, Teflon |
| piroxicam | methanol | PUR, polycarbonate, cellulose |
| phenylbutazone | chloroform, acetone | PDMS, PMMA |
| acetylsalicylic acid | ethanol | PMMA, polyester |
| glucocorticoids (steroids) | ethanol, methanol, acetone, chloroform, with the exception of triaminolone acetonide, which is well soluble in DMF | for swelling, almost all suitable polymers in the range of average cohesive energy densities may be used, since the steroids are amphiphilic materials |
| acetylsalicylic acid | ethanol | PUR, PMMA, polyester |
| isosorbide nitrate | chloroform, acetone | PDMS, Teflon, PMMA |
| nifedipin | chloroform, acetone | PDMS, Teflon, PMMA |
| verapamil | chloroform, acetone, ethyl acetate | PDMS, Teflon, PMMA, polyethylene |
| nadolol | methanol | PUR, polycarbonate, cellulose polyethylene terephthalate |
| metropolol | $H_2O$, ethanol | cellulose, PUR |
| pindolol | higher alcohols | PUR, polycarbonate, cellulose |

Further information concerning the selection of suitable partners is contained in EP-A-0 560 875.

Polyethylene terephthalate may also be transferred to the swollen state with selected solvents, such as acetone, benzaldehyde, dichloroethane, diphenyl ether, acetophenyl, THF, dioxane, $CHCl_3$, $CH_2Cl_2$. PET is employed, for example, for artificial vessels and heart valves.

Another efficient method comprises dissolving polymers using solvents, mixing with the pharmaceutical products, placing in a mold, and evaporating the solvent; this is called "solvent casting". The solvent casting technique has long been known. The release kinetics versus antimicrobial efficiency could be shown first in 1991 (3). This was possible with non-cross-linked polymers with solvents which are non-toxic and easily evaporated. Very high concentrations of the active substance can be achieved in the plastic material (1, 3, 5, 7 to 9). For achieving a long release time, in particular, a molecularly disperse distribution of a substance soluble in the polymer is suitable (7). Surface-bound active substances are less efficient (3, 8).

Another possibility for the preparation of the medical products according to the invention consists in preparing pharmaceutically active vascular prostheses in the form of flexible tubes or thin tubes by spinning fibers from polymer solutions (special form of solvent casting) containing the above mentioned active substances and conveying and laying the fibers on a rod-shaped substrate to form a web. Polyamides, polyacrylates and polyurethanes can be combined with lipophilic or. hydrophilic substances.

Further possibilities for incorporating or filling plastic materials with pharmaceuti-cally active substances are the extrusion or thermal injection molding of polymers. In this case, it is only possible to combine active substances with polymers having similarly high melting points and thermal resistance. The combination of active substances with plastic materials such as polyurethane, silicone, polyethylene terephthalate, polyethylene and other high-melting polymers is only possible for active substances which have a similarly high melting point (or thermal stability). This is the case, for example, with gentamicin sulfate. Lower melting plastic materials for melt extrusion and injection molding may be employed. These are preferably polymers which are thermoplastically processable in a range of 100° C.±30°. It is further possible to reduce the melting point of polymers by the addition of $CO_2$ gas in the extrusion and thus to add thermolabile substances.

The group of substances A includes, in particular, sparingly soluble salts or waxes. Examples of such components with low pharmacological activity which are released very slowly into the body fluids include non-ionic surfactants, such as acetylglycerides, diacetylglycerides, monoglycerides, diethylene glycol monostearate, ethylene glycol monostearate, glycol monostearate, compounds of monolauryl ethers, mono-di-glycerides, propylene glycol monostearate, sorbitol monostearate, palmitate, sesquioleate, tridecanate, tristearate, ionic surfactants, hyaluronic acid derivatives and phospholipids. These substances may improve the biocompatibility of a medical product. However, an active substance is preferred for substance A.

If substance A or substance B is to have antimicrobial properties, it has been found that rifampicin penetrates bacteria intracellularly and represents an efficient substance against biofilms (2). Other ansamycin derivatives having similar properties may also be used (rifamycin, rifapentin). Antimicrobial substances having lipophilic properties which have also found clinical use for so-called difficult-to-treat infections are preferably mentioned. In principle, all antimicrobially active groups may be used, such as lipophilic members of the group of aminoglycosides, of the group of cephalosporins and related β-lactams, chloramphenicol, lincosamides, macrolides, penicillins, quinolones, sulfonamides, tetracyclins, except for the combination tetracyclin-minocyclin. Preferred lipophilic antibiotics are benzathin, phenoxymethylpenicillin, chloramphenicol, chlortetracyclin, ciprofloxacin betain, ciprofloxacin, clarithromycin, clindamycin palmitate hydrochloride, trimethoprim, erythromycin 2-acetate, stearate; erythromycin estolate, erythromycin ethylsuccinate, erythromycin glutamate, lactopropionate, stearate, fusidinic acid, preferably free fusidinic acid, gramicidin, mupirocin, lipophilic members of the imidazole series, such as econazole, itraconazole, clotrimazole and others, pristinamycin, rifabutin, rifapentin, rifampicin, silver sulfadiazine, except for the combination silver sulfadiazine/chlorhexidine, sparfloxacin, teicoplanin or remoplanin, pristinamycin because of its lipophilic alkyl residue, and tyrothricin because of its water-insolubility.

Miconazole salicylate, sulfosalicylmiconazole and miconazole acetylsalicylate are especially mentioned as lipophilic components which can be prepared from the miconazole base. These substances are advantageous because they have antimicrobial and antithrombogenic activities. Other substances having antim-icrobial activity comprise lipophilic salts of silver. Silver salts in the inorganic form are extremely hydrophilic, diffuse badly in plastics, and thus the artisan does not obtain the desired slow-release system. Lipophilic salts or complexes of silver include combinations with acidic antibiotics, such as fusidinic. acid or mupirocin, or salicylic acid or simply the addition of, for example, longer-chain fatty acids from $C_2$ (=acetate) to $C_\infty$(=infinite). Thus, such lipophilized silver salts can diffuse better. The combination of the antiseptic 8-quinolinol, which can complex $Ag^+$ ions and is sparingly water-soluble in the form of Ag-quinolinol, is also possible. The combination of silver ($Ag^+$) with lipophilic antithrombotics having a $pK_a$ value in the acidic range is also possible. In addition, it is possible to combine silver with lipophilic complexing agents, such as EDTA and others. These include ethylenediamine tetraacetate, IGTA, DTPA (diethyltriaminepen-tanoic acid), DMSA, deferoximin, dimercaprol, diethylenetetramine. In principle, all chelates and salts are possible which can complex silver to yield a lipophilic component.

The combination with antiestrogens, antigestagens, gestagen or estrogen is also possible. In this case, it is convenient to modify blades which often consist of silicone sheets doped with sexual hormones and are subcutaneously implanted. They achieve the desired antifertility control by a controlled release. Moreover, these implants may be additionally protected with antimicrobially active substances in order to prevent infections.

Wound plasters made of polyurethane or silicone may also be modified, for example, with Ag salicylate and another lipophilic additive.

Further, it is possible to influence the release of hydrophilic antibiotics or other pharmaceutically effective substances in collagen webs by a lipophilic additive. In addition, it is also possible to sustain the release of disinfectants, such as chlorhexidine, octenidine, polyhexanide and irgasan, for urological use and thus to achieve a prolonged activity. Further, it is also possible to decelerate the release of antineoplastic agents, such as methotrexate, from bone cement with a lipophilic additive. In addition, it is also possible to sustain the release of prostaglandins with a lipophilic additive.

As the pharmaceutically active substances, especially as substance A, there may be further used analgetics, such as auranofin, benorylate, diclofenac (acid), diflunisal, flurbiprofen, ibuprofen, indomethacin, ketoprofen, naproxen, phenyl-butazone, and local anesthetics, such as amethocain, benzocain and butyl aminobenzoate. Especially soft or hard contact lenses can be modified with lipophilic antiphlogistics and local anesthetics, such as lidocain and xylocain.

Implants for glottis substitutes in laryngeal tumors can preferably be coated with imidazoles or nystatin.

Androgenic and anabolic steroids can be employed for gonadal disorders or in patients with delayed growth or puberty, or in females with breast cancer. Estrogens are locally administered in estrogen deficiency, for contraception and in menopausal or postmenopausal deficiency conditions, in males with prostatic neoplasias, and in females with breast cancer. Progesterones are employed in combination with estrogen in menstruation disorders. In addition, progesterones are employed in endometrial hyperplasias and cancer, and in hormonal contraception, for example, in the form of an active substance polymer depot.

Sustained release is possible, for example, with the following sparingly watersoluble active substances: algestones, acetophenide, allylestrenol, broperestiol, chlormadinone acetate, chlortrianisen, cyproterone, danzole, dinestrol, drostanolene propionate, dihydrogesterone, ethynolestradiol, ethynylestradiol, ethisterone, ethylestrenol, ethynol diacetate, fluoxymesterone, hydroxyprogesterone hexanate, lynestrinol, methoxyprogesterone acetate, megestrol acetate, metandienone, methyltestosterone, norethisterone acetate, estradiol and the derivatives of estradiol, such as estrado benzoate cypionate, dipropionate, enanthate, hexahydrobenzoate, phenylpropionate, undecanate, valerate and deconjugated estrogens, such as the esterified estrogens, estrones and others, from the androgen group, anabolic steroids, estrogens and progesterones.

Antithrombotically active substances include, for example, all heparin derivatives (optionally lipophilized), acetylsalicylic acid derivatives, ticlopidin, argatroban (CAS 73963-72-1), cloricromene (CAS 68206-94-0), clorindione (CAS 1146-99-2), nafazatram, trifliusal and the especially lipophilic dipyridamole.

The invention will be further illustrated by way of the following Examples.

EXAMPLE 1

Described is the preparation of a polyurethane film containing antitumor agents which are released from the medical plastic by controlled release, to which lipophiiic substances are added in order to sustain the release. The matrix, metalloproteinases or combretastatin or vascular-epithelial growth factor or thalidomid or squalamine or SU5416, a tyrosine kinase enzyme blocker, are dissolved in tetrahydrofurane and pellethane (10% pellethane, 1% substances, 89% solvent) in a ratio of 5% by weight to 5% by weight of miconazole nitrate by solvent casting. The polymer is cast in a mold together with the mixture of substances, slowly evaporated at 40° C., so that the solvent is completely evaporated, and a film is formed. The release of these substances as measured by HPLC exceeds a period of 30 days. After two days, a steady state release of 2 to 5 $\mu$g per substance per $cm^2$ of polymer surface is obtained.

EXAMPLE 2

A polyurethane catheter is swollen in ethyl acetate with 5% (w/w) rifampicin and 10% (w/w) clotrimazole at 30° C. for 10 minutes, so that the substances can diffuse into the expanded polymeric matrix. Then, the catheter is removed from the solution, evaporated at room temperature for 24 hours, then evaporated at reduced pressure and 50° C. for 48 hours, in order to extract any residual solvent from the plastic material.

Figure 1:
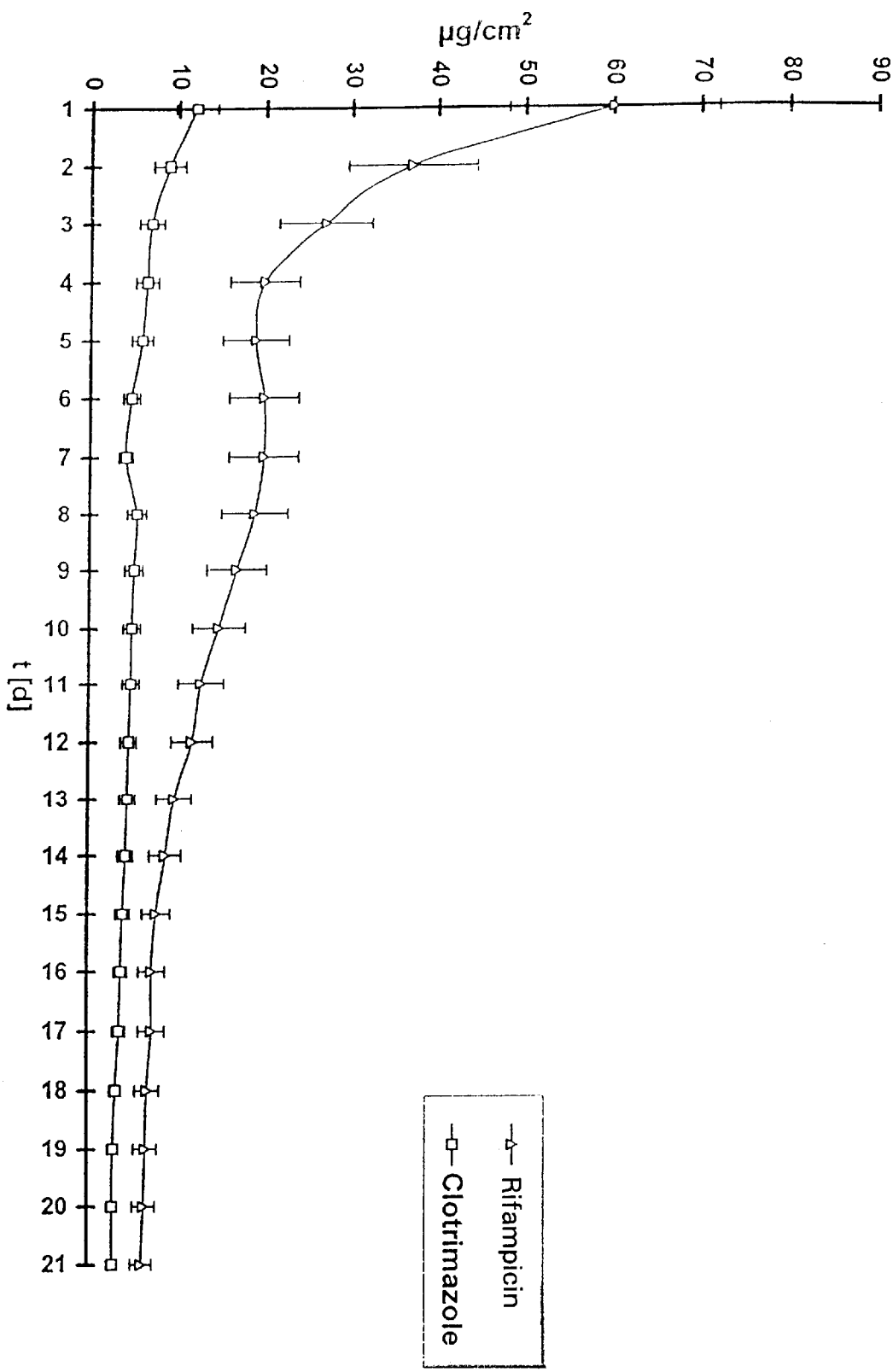
FIG. 1: Release of rifampicin/clotrimazole from catheter
Figure 2:
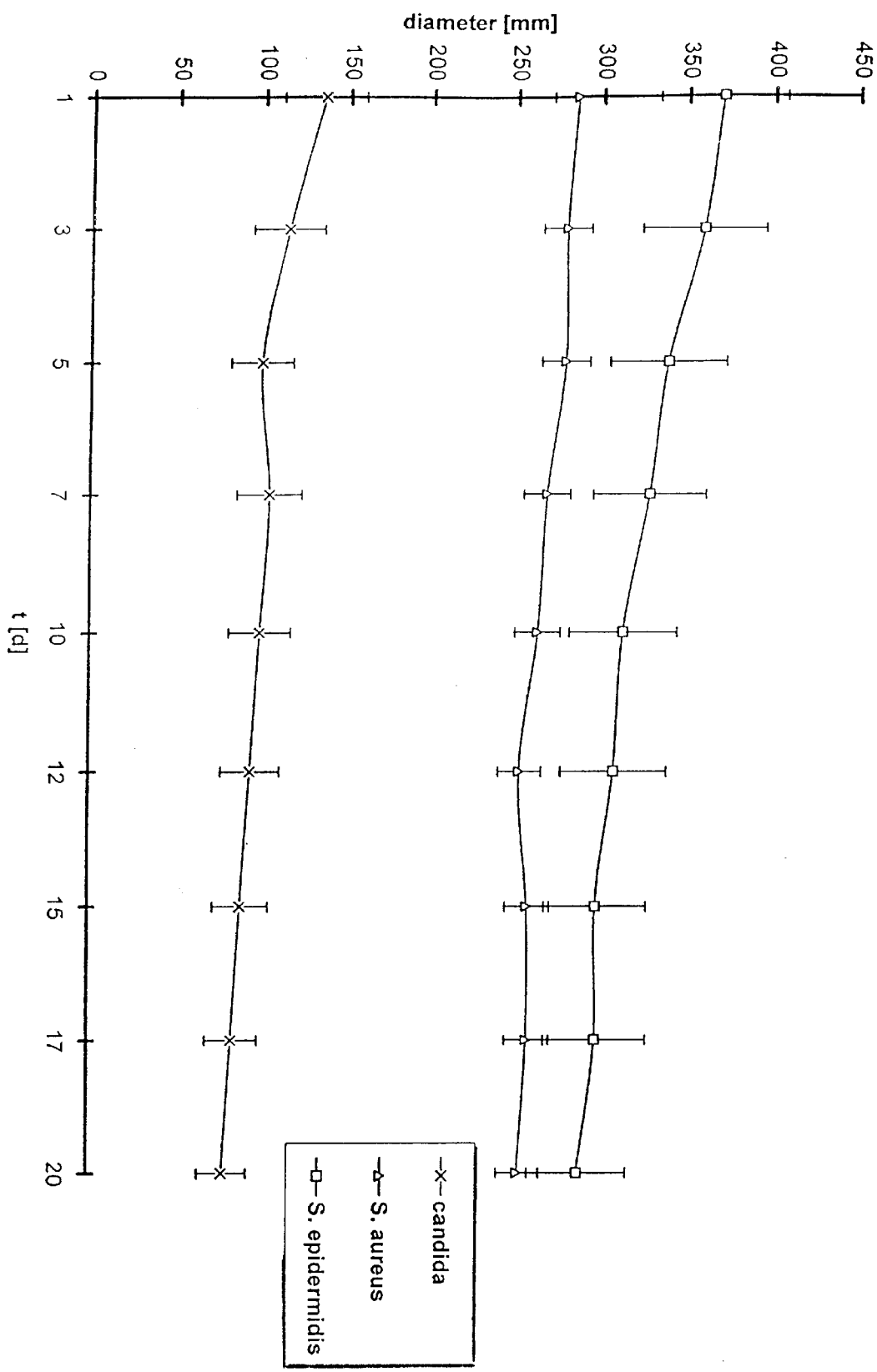
FIG. 2: Antimicrobial half-life in agar diffusion test against various bacterial species
Figure 3:
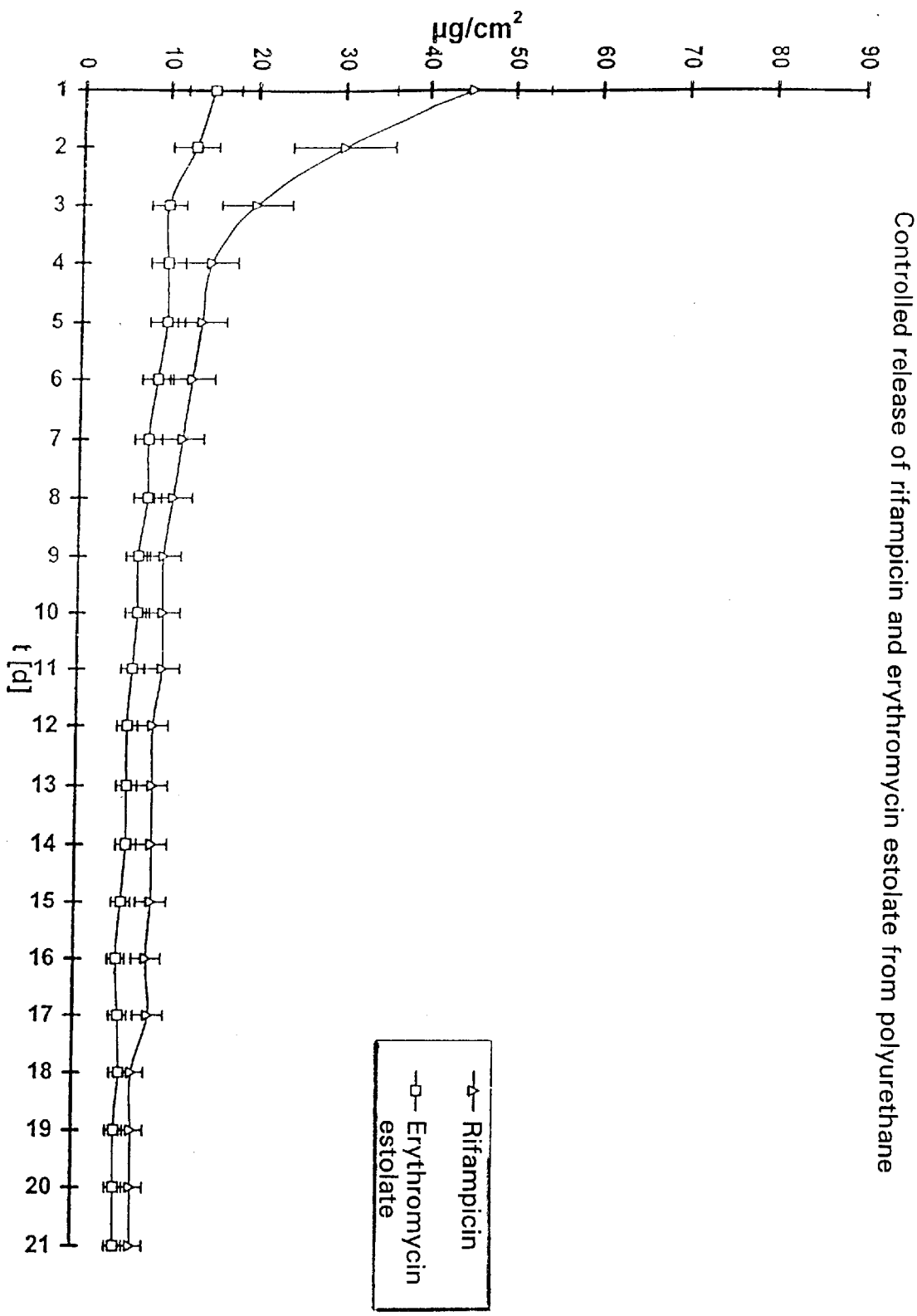
FIG. 3: Release of rifampicin/erythromycin estolate
Figure 4:
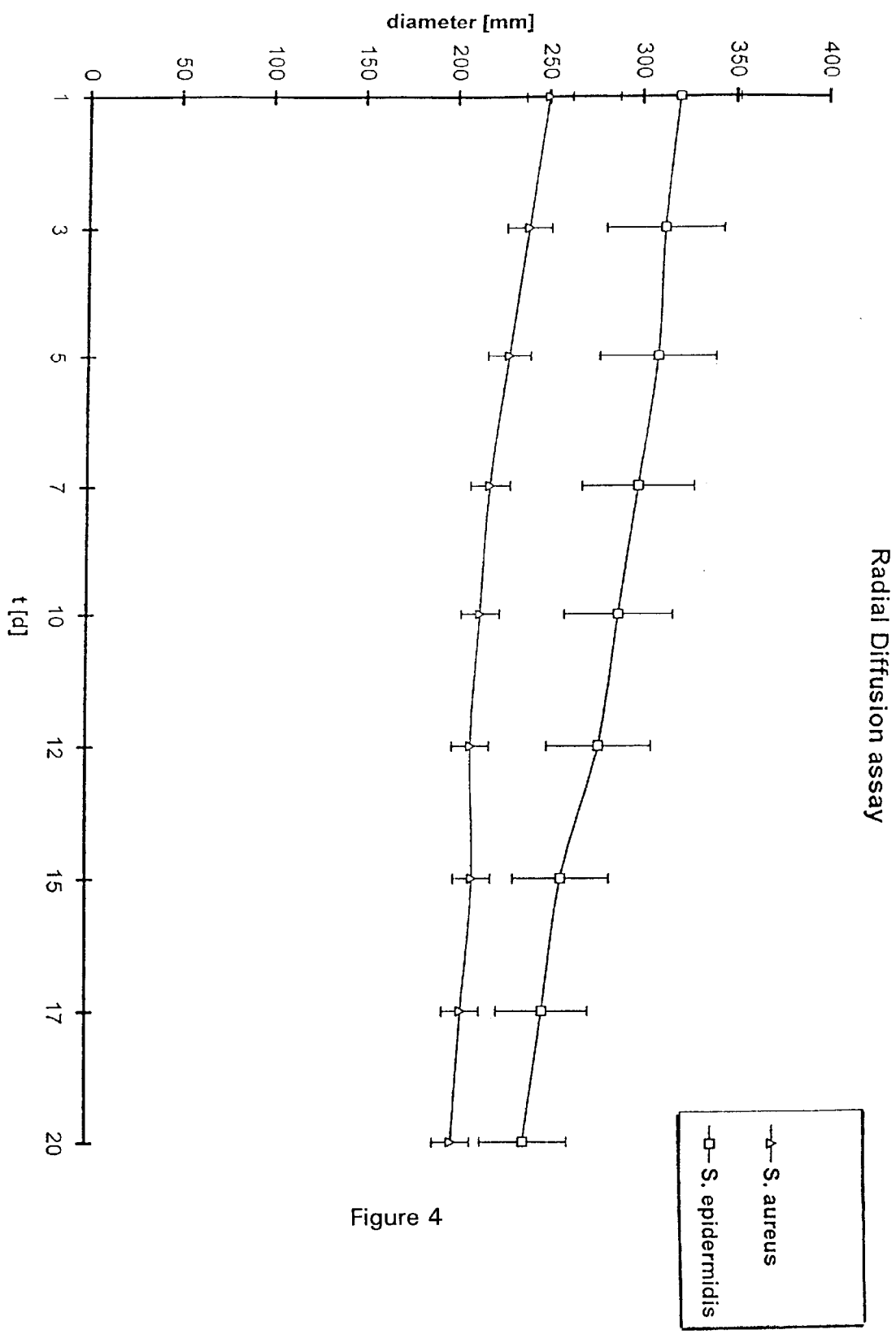
FIG. 4: Antimicrobial half-life in agar diffusion test (staphylococci)
Figure 5:
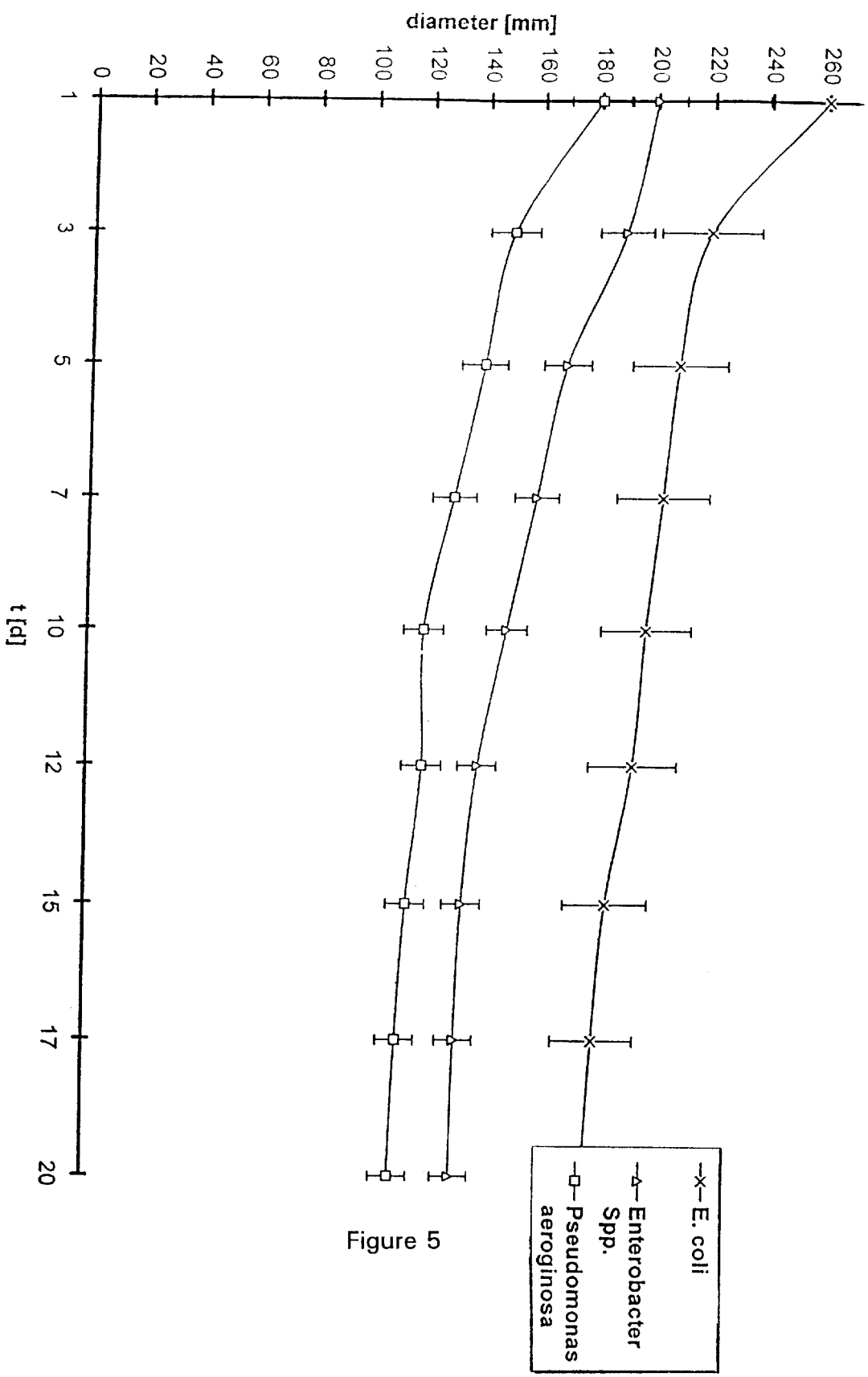
FIG. 5: Antimicrobial half-life in agar diffusion test (enterobactericeae)

This rifampicin/clotrimazole polyurethane coating is capable of efficiently releasing active substances for more than two months. The release curve of clotrimazole/rifampicin is shown in FIG. 1 in which the very much more water-soluble rifampicin obtains a similarly constant release pattern of almost zero order as clotrimazole through the lipophilic retention effect of clotrimazole after the initial burst effect of superficially bound active substances. This is possible only because the very sparingly water-soluble clotrimazole functions as a reservoir, covehicle and at the same time as a retention membrane for the more hydrophilic rifampicin. This is also possible with other substances, for example, fenticonazole or other imidazole derivatives, such as miconazole, sulfosalicylmiconazole, miconazolenitrate, miconazole salicyiate or miconazole acetylsalicylate and other miconazole derivatives. Other imidazole derivatives which are almost insoluble in water, such as ketoconazole, itraconazole, fenticonazole, econazole and others, are also possible. After three weeks of release, >80% of the active substance is still present in the implant material. The release profile can be approximated for more than three months.

EXAMPLE 3

Preparations of a Polyurethane Catheter by Means of Dichloromethane, Rifampicin and a Lipophilic Erythromycin Salt (Erythromycin Estolate)

The lipophilic erythromycin salt is almost insoluble in aqueous solutions, in contrast to the moderately water-soluble rifampicin. Pelethane catheters were swollen in a 5% rifampicin, 10% erythromycin solution in dichloromethane at 30° C. for 15 min, the swollen catheter was dried at room temperature for 24 hours, followed by evaporation at reduced pressure, 0.1 mbar, and 50° C. for 48 hours. This provides a slow release system with an incorporation content of 10% by mass in which the release of rifampicin was parallel with the slow release of the lipophilic erythromycin salt, similarly as in Example 2, after the burst effect. This lipophilic erythromycin salt again acts as an internal diffusion membrane.

EXAMPLE 4

Incorporation of the Amphiphilic Chlorhexidine Base and the Lipophilic Clindamycin Palmitate in Polyurethane by Solvent Casting The polyurethane is dissolved in tetrahydrofurane, and 5% chlorhexidine base and 5% of the sparingly soluble clindamycin salt are added to this solution. After stirring and raising the temperature to 60° C., this solution is cast in a mold, the solvent is slowly evaporated at reduced pressure, and later completely evaporated at 50° C. and reduced pressure. This active substance containing polyurethane film was capable of releasing active substances for more than two months, the lipophilic clindamycin salt sustaining the release of chlorhexidine base, resulting in a release of almost zero order.

EXAMPLE 5

Coating of a Total Endoprosthesis With a Miconazol Base/rifampicin Mixture

A total endoprosthesis coated with a 200 μm thick porous hydroxyapatite layer was placed in an acetone solution containing 5% rifampicin, 10% miconazole base for 5 minutes. Then, the prosthesis was removed and dried at room temperature for 24 hours. In order to enlarge the carrier layer, the prosthesis was immersed in the bath another two times for 5 seconds each and then dried. The coated prosthesis was eluted in phosphate buffer at 37° C. within 20 days. Miconazole base acted here as a reservoir and carrier for the more hydrophilic rifampicin. The combination of rifampicin with the sparingly soluble ciprofloxacin betain was also release-active for 14 days (not shown).

EXAMPLE 6

Polyurethane Urinary Tract Catheter With EDTA/clindamycin Coating for Preventing Incrustation and Infection To a 10% solution of polyurethane in tetrahydrofurane was added a 10% (based on the polymer) solution of EDTA and clindamycin palmitate. The solution was cast in a mold as in Example 4 and evaporated. Over a period of four weeks, the release of more than 2 μg/cm$^2$ of surface could be measured by HPLC.

EXAMPLE 7

Polyurethane Urinary Tract Catheter With Ag Salicylate and Tioconazole

A solution of 90% tetrahydrofurane, 9% PUR, 0.5% Ag salicylate and 0.5% tioconazole was stirred to homogeneity at 40° C. A polyurethane catheter was successively dipped in the solution for 20 seconds each and then dried. This procedure was repeated five times. After the second day of elution, the coated catheter showed a release of almost zero order over a period of 30 days.

References (1) Olanoff, L. S., Anderson, J. M., Jones, R. D.: Sustained release of gentamicin from prosthetic heart valves. Trans. Am. Soc. Artif. Intern. Organs 1979; 25: 334–338.
(2) Schierholz, J. M., Jansen, B., laenicke, L., Pulverer, G.: In vitro efficacy of an antibiotic releasing silicone ventricle catheter to prevent shunt infection. Biomat. 1994; 15: 996–1000.
(3) Schierholz, J. M., Jansen, B., Steinhauser, H., Peters, G., Schuhmacher-Perdreau, F., Pulverer, G.: Drug release from antibiotic-containing polyurethanes. New Polymeric Matter 1990; 3: 61–72.
(4) Schierholz, J. M., Rump, A. F. E., Pulverer, G.: Drug delivery concepts for efficacious prevention of foreign-body infections. Zbl. Bakt. 1996; 284: 390–401.
(5) Schierholz, J. M., Rump, A. F. E., Pulverer, G.: Ciprofloxacin containing polyurethanes as potential drug delivery systems to prevent foreign-body infections. Drug Res. 1997; 47 (I), 1: 70–74.
(6) Schierholz, J. M.: Physico-chemical properties of a rifampicin-releasing polydimethyl-siloxane shunt. Biomat. 17: 1997.
(7) Schierholz, J. M., Steinhauser, H., Rump, A. F. E., Berkels, R., Pulverer, G.: Controlled release of antibiotics from biomedical polyurethanes: morphological and structural features. Biomat. 18: 1997.
(8) Sherertz, R. J., Carruth, W. A., Hampton, A. A., Byron, M. P., Solomon, D. D.: Efficacy of antibiotic-coated catheters in preventing subcutaneous staphy-lococcus aureus infection in rabbits. J. Inf. Dis. 1993; 167: 98–106.
(9) Solomon, D. D., Sherertz, R. J.: Antibiotic releasing polymers. J. Contr. Rel. 1987: 343–352.

What is claimed is:

1. A non-degradable medical implant comprising a support material and monolithic distribution of at least two substances or groups of substances molecularly dispersed throughout a polymeric matrix, the at least two substances having different degrees of hydrophilicity for retarded release, of which the first is referred to as substance A and the second is referred to as substance B, substance A being more lipophilic than substance B, wherein substance A has a solubility w/w in water of from 300 μg/ml to 1 μg/ml, substance B has a higher solubility than that of substance A, at least one of substances A and B is a pharmaceutically active substance, and wherein the amount of substance A or B is respectively from at least an effective amount to 10% by weight, based on the weight of the support material.

2. The medical implant according to claim 1, characterized in that substance A is a pharmaceutically active substance.

3. The medical implant according to claim 1, characterized in that substance B is a pharmaceutically active substance.

4. The medical implant according to claim 2, characterized in that substance B is a pharmaceutically active substance.

5. The medical implant according to claim 1, characterized in that said medical product is made of a material selected from siloxane, polyurethane, acrylates, polycarbonates, cellulose, cellulose derivatives, polymers of tetrafluoroethylene, polyethylene terephthalate and hydrogels, and endoprostheses.

6. The medical implant according to claim 2, characterized in that said medical product is made of a material selected from siloxane, polyurethane, acrylates, polycarbonates, cellulose, cellulose derivatives, polymers of tetrafluoroethylene, polyethylene terephthalate and hydrogels, and endoprostheses.

7. The medical implant according to claim 3, characterized in that said medical product is made of a material selected from siloxane, polyurethane, acrylates, polycarbonates, cellulose, cellulose derivatives, polymers of tetrafluoroethylene, polyethylene terephthalate and hydrogels, and endoprostheses.

8. The medical implant according to claim 4, characterized in that said medical product is made of a material selected from siloxane, polyurethane, acrylates, polycarbonates, cellulose, cellulose derivatives, polymers of tetrafluoroethylene, polyethylene terephthalate and hydrogels, and endoprostheses.

9. The medical implant according to claim 1, wherein the substances are selected from the group consisting of lipophilic members of the group of aminoglycoside salts, of the group of cephalosporins and related β-lactams, chloramphenicol, lincosamides, macrolides, penicillins, quinolones, sulfonamides, lipophilic salts of silver, DMSA, deferoximin, dimercaprol, diethylenetetramine, lipophilic heparin derivatives, lipophilized acetylsalicylic acid derivatives, ticlopidin, argatroban, cloricromene, clorindione, nafazatram, triflusal and dipyridamole, gramidicin, pristinamycin, tyrothricin, hiclosan, octinidin and combinations thereof.

10. The medical implant according to claim 1 characterized in that the substances are hormones selected from the group consisting of antiestrogens, antigestagens, gestagen or estrogen, algestones, acetophenide, allylestrenol, broperestiol, chlormandinone acetate, chlortrianisen, cyproterone, danzole, dinestrol, drostanolene propionate, dihydrogesterone, ethynolestradiol, ethynylestradiol, ethisterone, ethylestrenol, ethynol diacetate, fluoxymesterone, hydroxyprogesterone hexanate, lynestrinol, methoxyprogesterone acetate, megestrol acetate, methandienone, methyltestosterone, norethisterone acetate, estradiol and the derivatives of estradiol, from the androgen group, anabolic steroids, enzymes progesterones, wherein the derivatives of estradiol are selected from the group consisting of estrado benzoate cypionate, dipropionate, enanthate, hexahydrobenzoate, phenylpropionate, undecanate, valerate, deconjugated estrogens and combinations thereof.

11. The medical implant according to claim 1, wherein component A is a lipophilic antibiotic selected from the group consisting of benzathin, phenoxymethylpenicillin, chloramphenicol, chlortetracycline, ciprofloxacin betain, clarithromycin, clindamycin palmitate hydrochloride, clindamycin stearate hydrochloride, trimethoprim, erythromycin 2-acetate, stearate; erythromycin estolate, erythromycin ethylsuccinate, erythromycin glutamate, lactopropionate, stearate, fusidinic acid, gramicidin, mupirocin, and lipophilic members of the imidazole series, and combinations thereof.

12. The medical implant according to claim 11, wherein the lipophilic members of the imidazole series are selected from the group consisting of econazole, itraconazole, clotrimazole, sulfosalicylmiconazole, miconazole salicylate, miconazole acetylsalicylate, free miconozole and combinations thereof.

13. The medical implant according to claim 1, characterized in that substance B is selected from the group consisting ofphospholipids, hyaluronic acid derivatives, and combinations thereof.

14. The medical implant product according to claim 1, characterized in that the pharmaceutically active substance is capable of becoming intracellularly enriched in bacteria, platelets, and/or other cell types.

15. The medical implant according to claim 14, characterized in that said pharmaceutically active substance is selected from the group consisting of rifampicin, erythromycin, fusidinic acid, imidazole or clindamycin derivatives, mupirocin, quinolone derivatives, ticlopidin.

16. A non-degradable medical product for implantation comprising a support material and monolithic distribution of at least two substances or groups of substances molecularly dispersed throughout a polymeric matrix, the at least two substances having different degrees of hydrophilicity for retarded release, of which the first is referred to as substance A and the second is referred to as substance B, substance A being more lipophilic than substance B, wherein substance A has a solubility w/w in water of from 300 $\mu$g/ml to 1 $\mu$g/ml, substance B has a higher solubility than that of substance A, at least one of substances A and B is a pharmaceutically active substance, and wherein the amount of substance A or B is respectively from at least an effective amount to 10% by weight, based on the weight of the support material.

17. The medical product according to claim 16, characterized in that substance A is a pharmaceutically active substance.

18. The medical product according to claim 16, characterized in that substance B is a pharmaceutically active substance.

19. The medical product according to claim 17, characterized in that substance B is a pharmaceutically active substance.

* * * * *